(12) United States Patent
Wakayama

(10) Patent No.: US 11,179,414 B2
(45) Date of Patent: Nov. 23, 2021

(54) METHOD FOR PRODUCING PROTEASE DEGRADATION COMPOSITION

(71) Applicant: LAIMU CORPORATION, Yokohama (JP)

(72) Inventor: Sachio Wakayama, Yokohama (JP)

(73) Assignee: LAIMU CORPORATION, Kanagawa (JP)

( * ) Notice: Subject to any disclaimer, the term of this patent is extended or adjusted under 35 U.S.C. 154(b) by 313 days.

(21) Appl. No.: 16/375,986

(22) Filed: Apr. 5, 2019

(65) Prior Publication Data

US 2019/0307788 A1 Oct. 10, 2019

(30) Foreign Application Priority Data

Apr. 6, 2018 (JP) .............................. JP2018-073686

(51) Int. Cl.

| | | |
|---|---|---|
| *A61K 31/728* | (2006.01) | |
| *C08B 37/08* | (2006.01) | |
| *C07D 307/62* | (2006.01) | |
| *A61K 31/341* | (2006.01) | |
| *C12N 9/50* | (2006.01) | |
| *A61P 17/02* | (2006.01) | |
| *A61K 38/00* | (2006.01) | |
| *A61K 9/00* | (2006.01) | |
| *A61K 31/38* | (2006.01) | |
| *A61P 17/16* | (2006.01) | |

(52) U.S. Cl.
CPC .......... *A61K 31/728* (2013.01); *A61K 9/0053* (2013.01); *A61K 31/341* (2013.01); *A61K 31/38* (2013.01); *A61K 38/005* (2013.01); *A61P 17/02* (2018.01); *A61P 17/16* (2018.01); *C07D 307/62* (2013.01); *C08B 37/0072* (2013.01); *C12N 9/50* (2013.01)

(58) Field of Classification Search
None
See application file for complete search history.

(56) References Cited

U.S. PATENT DOCUMENTS 6,476,005 B1 * 11/2002 Petito .................... A61K 38/39
424/499
2008/0317730 A1 * 12/2008 Gennero ................ A61K 8/447
424/94.5

FOREIGN PATENT DOCUMENTS

| JP | 01175998 A | 7/1989 |
| JP | 2002145800 A | 5/2002 |
| JP | 2002223726 A | 8/2002 |
| JP | 6279801 B1 | 2/2018 |

OTHER PUBLICATIONS

Maurice et al., "Sexual difference in ascorbic acid synthesis, tissue ascorbic acid and plasma total antioxidant capacity in mature chickens" British Poultry Science vol. 48 No. 4 pp. 519-523 (Year: 2007).*
Boskovic-Rakocevic et al., "Effect of nitrogen fertilization on carrot quality" African Journal of Agricultural Research vol. 17 No. 18 pp. 2884-2900 (Year: 2012).*
Jacobson et al., "Effect of testosterone on ascorbic acid synthesis in rooster comb" Biochimica et Biophysica Acta, General Subjects vol. 237 No. 3 pp. 490-493 (Year: 1971).*
Japanese patent application No. 2018-073686, Office Action dated Jul. 10, 2018 with its English Translation.
Japanese patent application No. 2018-073686. Office Action dated May 15, 2018 with its English Translation.
Yamamoto, "Course in development of a stable vitamin C derivative (AA-2G)", Folia pharmacologica Japonica, pp. 160-165, vol. 132 (2008)—in Japanese.

* cited by examiner

*Primary Examiner* — Eric Olson
(74) *Attorney, Agent, or Firm* — Browdy and Neimark, PLLC

(57) ABSTRACT

Disclosed is a method for producing a protease degradation composition by degrading a composition containing a hyaluronic acid and a protein with a protease, in the presence of an ascorbic acid, an ascorbate or a salt thereof. The composition produced according to the method has a high fibroblast proliferation promoting effect and a high collagen production promoting effect.

7 Claims, 1 Drawing Sheet

METHOD FOR PRODUCING PROTEASE DEGRADATION COMPOSITION

BACKGROUND

Technical Field

The present invention relates to a method for producing a protease degradation composition.

Description of Related Art

Hyaluronic acid is known to have an action of enhancing a moisturizing effect and a water-retentive effect, and has heretofore been incorporated in various cosmetics and medicines. For example, hyaluronic acid is generally used by directly applying it to a dry skin or a rough skin so as to enhance the moisture-retaining property thereof for skin conditioning, or for preventing moisture from being lost from the skin surface in a dry season, hyaluronic acid is preventively applied to the skin surface. In addition, hyaluronic acid is expected to express a function derived from the moisturizing effect thereof or any other useful characteristics than the moisturizing effect, and some studies are known relating to new use thereof.

For example, Patent Document 1 proposes use of a degradation product produced by degrading a composition containing a hyaluronic acid and a protein with a protease, as a wound treatment agent. The wound treatment agent uses a hyaluronic acid and a protein that are biogenic substances, and a slow-reacting enzyme, and is therefore highly safe, and can quickly treat a wound, for example, through oral administration or direct administration to a region of wound.

CITATION LIST

Patent Documents

Patent Document 1: JP-2002-145800A

SUMMARY

As described above, a degradation product produced by degrading a composition containing a hyaluronic acid and a protein with a protease has been proposed as a wound treatment agent.

On the other hand, fibroblasts are known as biological cells that play an important role in a wound healing process. Fibroblasts are a type of cells that constitute connective tissue, and when a skin is damaged, they migrate to the damaged part to grow proliferously thereby producing an extracellular matrix such as collagen, that is, fibroblasts play such an important role in a wound healing process. Accordingly, those capable of promoting the growth of fibroblasts are expected to have a high wound healing effect.

However, when the present inventors added the above-mentioned protease degradation product of a composition containing a hyaluronic acid and a protein to a culture medium of fibroblasts and investigated the condition of the cell growth therein, the growth of the fibroblasts could not almost be promoted (see Examples given hereinunder).

Accordingly, for solving the problems in the existing technology, the present inventors have promoted investigations for the purpose of providing a composition having a high fibroblast proliferation-promoting effect and having a high fibroblast collagen production-promoting effect. In addition, the inventors have further promoted investigations for providing a method for producing such a composition at low cost.

The present inventors have made assiduous studies for the purpose of solving the above-mentioned problems and, as a result, have found that, in degrading a composition containing a hyaluronic acid and a protein with a protease, when an ascorbic acid, an ascorbate or a salt thereof is made to exist in the composition, then a degradation composition having a fibroblast proliferation-promoting effect and a collagen production-promoting effect that are noticeably higher than those of a protease degradation product prepared in the absence of such an ascorbic acid, an ascorbate or a salt thereof can be obtained. With that, the present inventors have further found that, utilizing the effect of the protease degradation composition, a fibroblast proliferation agent and a collagen production promoter that are highly safe can be provided. The present invention has been proposed based on these findings, and specifically has the following constitution.

[1] A method for producing a protease degradation composition by degrading a composition containing a hyaluronic acid and a protein with a protease, in the presence of an ascorbic acid, an ascorbate or a salt thereof.

[2] The production method according to [1], wherein the composition containing a hyaluronic acid and a protein is a comb.

[3] The production method according to [1] or [2], wherein as the ascorbic acid, ascorbate or salt thereof, one in which the hydrogen atom of the 2-positioned hydroxy group is substituted with a glycosyl group is used.

[4] The production method according to any one of [1] to [3], including a step of adding the ascorbic acid, ascorbate or salt thereof to the composition.

[5] The production method according to [4], wherein the amount of the ascorbic acid, ascorbate or salt thereof added to the composition is 0.5 to 40% by mass relative to the total amount of the composition after the addition.

[6] The production method according to [4] or [5], wherein the ascorbic acid, ascorbate or salt thereof is added before the composition is brought into contact with a protease.

[7] The production method according to [6], in which the composition containing a hyaluronic acid and a protein is a comb, and which includes:
a step of chipping the comb into pieces of 0.5 cm square or more, a step of adding an ascorbic acid, an ascorbate or a salt thereof to the comb pieces and mixing them to give a mixture, and a step of adding a protease to the mixture to thereby degrade the comb pieces with the protease.

[8] A composition produced according to the production method of any one of [1] to [7].

[9] The composition according to [8], wherein the content of the ascorbic acid, ascorbate or salt thereof is 0.5 to 40% by mass.

[10] A fibroblast proliferation promoter containing the composition of [8] or [9].

[11] A collagen production promoter containing the composition of [8] or [9].

According to the production method for a protease degradation composition of the present invention, a protease degradation composition having a high fibroblast proliferation promoting effect and a high fibroblast collagen production promoting effect can be produced at low cost. The composition of the present invention has a high fibroblast proliferation promoting effect and a high collagen production promoting effect, and therefore can be effectively used as a fibroblast proliferation agent and a collagen production promoter.

DETAILED DESCRIPTION OF THE INVENTION

Figure 1:
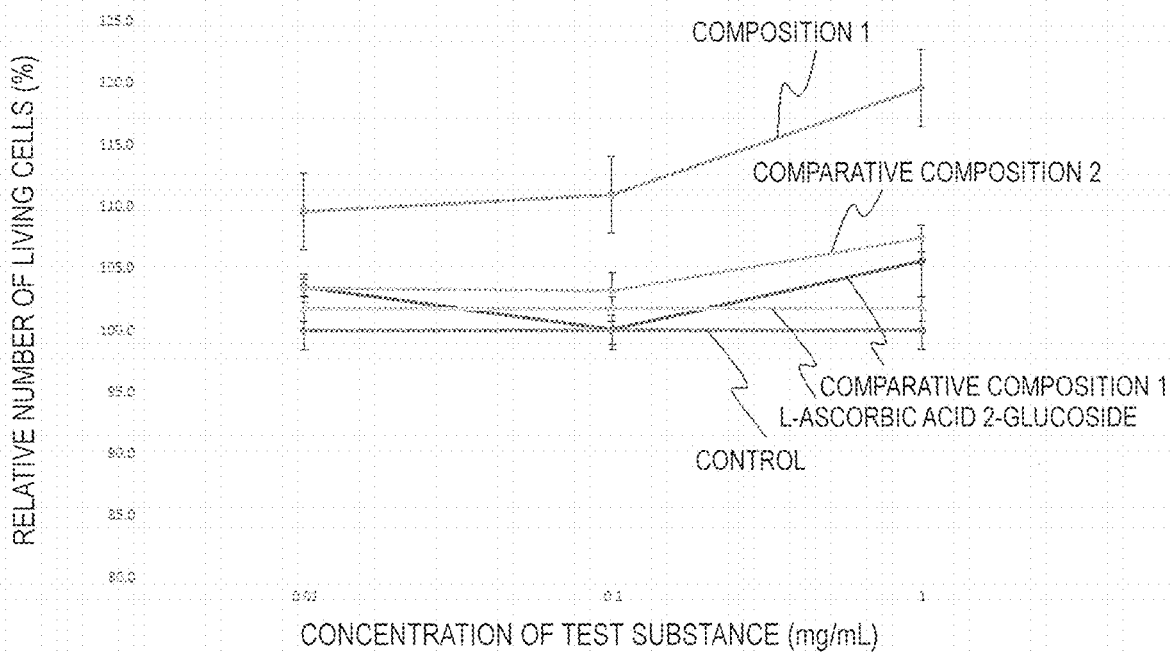
FIG. 1 is a graph showing a relative number of living cells after culture of human fibroblasts for 1 day in a medium added with the composition 1, the comparative composition 1 or 2 or L-ascorbic acid 2-glucoside.

The present invention is described in detail hereinunder. The description of the constitutive elements of the invention given hereinunder is for some typical embodiments or examples of the invention, to which, however, the invention should not be limited. In this description, the numerical range expressed by the wording "a number to another number" means the range that falls between the former number indicating the lower limit of the range and the latter number indicating the upper limit thereof.

<Production Method for Protease Degradation Composition>

The production method for a protease degradation composition of the present invention is characterized by degrading a composition containing a hyaluronic acid and a protein with a protease, in the presence of an ascorbic acid, an ascorbate or a salt thereof.

In the production method of the present invention, it is considered that the ascorbic acid, ascorbate or salt thereof made to exist in the reaction system would have an effect advantageous for the degradation of the composition with a protease, and the resultant protease degradation composition has a high fibroblast proliferation promoting effect and can effectively promote collagen production by fibroblasts.

In the following, the composition for use in the production method of the present invention, the ascorbic acid, ascorbate or salt thereof and the condition of adding them, and the protease are described. In the following description, the effect of promoting collagen production by fibroblasts is simply referred to as "collation production promoting effect".

[Composition]

First described is the composition to be used as a raw material for the protease degradation composition in the present invention.

With no specific limitation, the hyaluronic acid contained in the composition may be any hyaluronic acid that is generally used as a component for cosmetics and medicines. Originally, a hyaluronic acid is isolated from a bovine vitreous body, but not limited thereto, any one isolated from an animal joint fluid or a cock's comb is usable here. Not one isolated from the natural field but any other obtained by synthesis or according to microbial fermentation may also be usable.

Hyaluronic acid is a complicated polysaccharide of amino acids and uronic acids, and the details of the structure are not specifically limited. For example, there can be mentioned a polysaccharide having a recurring unit of dioses of D-glucuronic acid and N-acetyl-D-glucosamine. The molecular weight of the hyaluronic acid contained in the composition is not specifically limited, and for example, the hyaluronic acid extracted from a cock's comb has a molecular weight of 6,000,000 to 10,000,000, but the hyaluronic acid extracted from a cock's comb has a mean molecular weight of hundreds of thousands to millions as it is degraded in the extraction process. The hyaluronic acid for use in the present invention may be an induced one or a thermally-denatured one so far as it does not too excessively lose the fibroblast proliferation promoting effect and the collagen production promoting effect of the protease degradation product to be obtained in the present invention. Compounds known as so-called hyaluronic acid derivatives can be effectively used in the present invention.

The protein contained in the composition may be any one irrespective of the kind thereof, but is extremely preferably a protein contained in a comb. The kind of the comb is not specifically limited, but using a cock's comb is preferred. A cock's comb contains a hyaluronic acid and is therefore advantageous in that any additional hyaluronic acid does not need to be separately added thereto in providing the composition (composition containing a hyaluronic acid and a protein) for use for producing the composition of the present invention. Consequently, when a cock's comb is used, the production process for the protease degradation composition of the present invention can be simplified and the production cost can be thereby reduced.

The composition for use in the present invention may contain only a protein and a hyaluronic acid, but may contain any other component, solvent or dispersion medium. The solvent and the dispersion medium may be any one capable of dissolving a protein and a hyaluronic acid, and water and an aqueous buffer are favorably used. The composition may be a natural substance itself containing a protein and a hyaluronic acid. The natural substance to be the composition includes an animal joint fluid and a comb, and a cock's comb is especially preferred as rich in a hyaluronic acid.

[Ascorbic Acid, Ascorbate or Salt Thereof]

In the present invention, the above-mentioned composition containing a hyaluronic acid and a protein is degraded with a protease to produce a protease degradation product, and the present invention is characterized in that, during the degradation reaction, an ascorbic acid, an ascorbate or a salt thereof is made to exist in the composition. With that, the resultant protease degradation composition of the present invention has a higher fibroblast proliferation promoting effect and a higher collagen production promoting effect as compared with a protease degradation product prepared from the composition not added with such an ascorbic acid, an ascorbate or a salt thereof.

The ascorbic acid for use in the present invention may be an L-ascorbic acid represented by the following formula, or may be an isomer of L-ascorbic acid. The isomer of L-ascorbic acid includes D-ascorbic acid, L-araboascorbic acid, and D-araboascorbic acid (also referred to as erythorbic acid or isoascorbic acid).

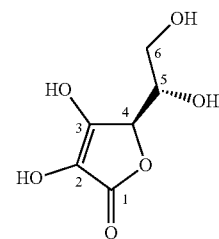 [SMILES: O=C1O[C@H]([C@@H](O)CO)C(O)=C1O]

In the formula, 1 to 6 each indicates the position number of L-ascorbic acid.

The ascorbate is an ascorbic acid derivative containing an ester bond formed through dehydration condensation (esterification) of the hydroxy group in an ascorbic acid with an acid. The ascorbate may be an L-ascorbate, or may also be an ester of an isomer that is prepared by esterifying an isomer of the above-mentioned L-ascorbic acid. Ascorbic acid has a hydroxyl group at the 2-position, the 3-position, the 5-position and the 6-position, in which any of these hydroxy groups may form an ester bond with an acid, and 2 or more hydroxy groups each may form an ester bond with an acid. The type of ascorbates includes a carboxylate, a phosphate, a nitrate, a sulfate, a borate and a sulfonate, and a carboxylate and a phosphate are preferred.

In a carboxylate of ascorbic acid, preferably, the carbon number of the acyl group is 1 to 20, more preferably 10 to 18, and even more preferably 14 to 16. The carboxylate is preferably such that the 6-positioned hydroxy group of ascorbic acid forms an ester bond with a carboxylic acid, that is, a 6-O-acylascorbic acid is preferred, and 6-O-palmitoylascorbic acid (ascorbyl 6-palmitate) is especially preferred.

In a phosphate of ascorbic acid, the phosphate group may be a monophosphoryloxy group, or may also be a phosphate group having a structure with plural phosphate groups linking thereto, such as a pyrophosphoryl group, a triphosphoryl group or a polyphosphoryl group. The phosphate is preferably such that the 2-positioned hydroxy group of ascorbic acid is converted into a phosphate group, and is more preferably one where the 2-positioned hydroxy group of ascorbic acid is converted into a monophosphoryloxy group, that is, ascorbyl 2-phosphate.

The ascorbic acid or ascorbate for use in the present invention may be one where the hydrogen atom of the hydroxy group is substituted with a substituent. The substituent includes an alkyl group such as an ethyl group, an aryl group such as a phenyl group, and a glycosyl group, a phosphate group, a sulfate group, and an alkenyl group. Specific examples of the glycosyl group include a glucopyranosyl group such as an α-D-monoglucopyranosyl group, a β-D-monoglucopyranosyl group; and a galactopyranosyl group such as a β-D-monogalactopyranosyl group. The hydroxy group of which the hydrogen atom is substituted with such a substituent may be at any of a 2-position, a 3-position, a 5-position and a 6-position (provided that, in an ascorbate, the hydroxy group to form an ester bond is excluded), and the hydrogen atoms of 2 or more hydroxy group may be substituted with substituents. For example, the hydroxy group of which the hydrogen atom is substituted with an alkyl group is preferably a 3-positioned hydroxy group, and the hydroxy group of which the hydrogen atom is substituted with a glycosyl group is preferably a 2-positioned hydroxy group. Preferred examples of ascorbic acids where the hydroxy group is substituted with a substituent include 3-O-ethylascrobic acid, L-ascorbic acid 2-glucoside (2-O-α-D-glucopyranosyl L-ascorbate).

Also preferably, the ascorbate for use in the present invention is a carboxylate of an L-ascorbic acid represented by the following general formula (1).

General Formula (1)

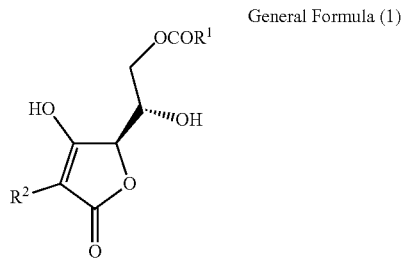

In the general formula (1), $R^1$ represents an alkyl group $(C_nH_{2n+1})$, $R^2$ represents a hydroxy group or a substituent.

n in the alkyl group $(C_nH_{2n+1})$ of $R^1$ is preferably 8 or more, more preferably 10 or more, and even more preferably 12 or more. Preferred examples of the alkyl group include a nonyl group $(C_9H_{19})$, an undecyl group $(C_{11}H_{23})$, a tridecyl group $(C_{13}H_{27})$, and a pentadecyl group $(C_{15}H_{31})$. Accordingly, the acyl group $(COR^1)$ is preferably a decanoyl group having 10 carbon atoms, a dodecanoyl group having 12 carbon atoms, a tetradecanoyl group having 14 carbon atoms, and a hexadecanoyl (palmitoyl) group having 16 carbon atoms.

The substituent of $R^2$ includes a glycosyl group, a phosphate group, a sulfate group, an alkyl group, an alkenyl group, and a phenyl group. For specific examples of the glycosyl group, referred to are the specific examples of the glycosyl group with which the hydroxyl group of the above-mentioned ascorbic acid and others may be substituted; and for specific examples of the phosphate group, referred to are the specific examples of the phosphate group in the above-mentioned phosphates.

Salts of an ascorbic acid or an ascorbate for use in the present invention may be salts with an inorganic ion or salts with an organic ion, but are preferably less toxic. The inorganic ion to form a salt with an ascorbic acid or an ascorbate includes various cations of an alkali metal (e.g., sodium, potassium), an ammonium ion, an alkaline earth metal (e.g., calcium, magnesium, strontium, barium), and aluminum. The organic ion to form a salt with an ascorbic acid or an ascorbate includes cations to be formed from organic bases such as trimethylamine, triethylamine, pyridine, picoline, N,N-dibenzylethylenediamine, ethanol amine, diethanolamine, trishydroxymethylaminomethane, and dicyclohexylamine. In particular, the ascorbic acid or ascorbate for use herein preferably forms a salt with a cation such as sodium, potassium, magnesium, calcium or aluminum among them.

Here, the ascorbic acid or ascorbate may form a salt with only one kind of cations mentioned above, or may form a salt with two or more kinds thereof. In the ascorbic acid or ascorbate, the position to be an anion part is not specifically limited, and for example, the proton at the 3-positioned hydroxy group may be dissociated to form an anion, or in the case where an acidic substituent is introduced, the proton of the acidic substituent may be dissociated to form an anion.

Among these ascorbic acids and ascorbates, ascorbic acid, L-ascorbic acid 2-glucoside, L-ascorbic acid 6-palmitate and salts thereof are preferred as these are used as food additives, and above all, L-ascorbic acid 2-glucoside and salts thereof are especially preferred as they hardly color compositions. In addition, from the viewpoint of high safety, so-called stable ascorbic acid derivatives such as L-ascorbic acid 2-glucoside, ascorbyl 2-phosphate and 3-O-ethylascrobic acid, and salts thereof are preferred.

[Condition in Adding Ascorbic Acid, Ascorbate or Salt Thereof]

In the present invention, a composition containing a hyaluronic acid and a protein is degraded with a protease in the presence of the above-mentioned ascorbic acid, ascorbate or salt thereof.

Specifically, for example, an ascorbic acid, an ascorbate or a salt thereof is added to and mixed with the composition, and the composition is degraded with a protease in the presence of the added substance. Here, when the composition is liquid, an ascorbic acid, an ascorbate or a salt thereof may be directly added to and mixed with the composition or a pulverized material of the composition, or the composition is dissolved in a solvent to give a solution or the composition of a pulverized material of the composition is suspended in a dispersion medium, and an ascorbic acid, an ascorbate or a salt thereof may be added to and mixed with the resultant solution or suspension. The ascorbic acid, ascorbate or salt thereof to be added to the composition may be a solid or a solution. The solvent to be used for the solution may vary depending on the kind of the ascorbic acid, ascorbate or salt thereof, and water or ethanol may be used. One alone of these may be added to the ascorbic acid, ascorbate or salt, or two or more thereof may be added thereto in combination.

The timing at which an ascorbic acid, an ascorbate or a salt thereof is added to the composition is before the end of the degradation reaction with a protease, and is preferably before the start of the degradation reaction and 1 minute before the end of the reaction, more preferably before the start of the degradation reaction and 5 minutes before the end of the reaction, and even more preferably before the start of the degradation reaction and 10 minutes before the end of the reaction. Here, before the start of the degradation reaction specifically means before the composition is brought into contact with a protease, and the end of the reaction means the end of the degradation process with a protease. It is considered that the ascorbic acid, ascorbate or salt thereof added at the timing mentioned above could bring about an advantageous effect for the degradation of the composition with a protease. As a result, the resultant protease degradation composition can have a high fibroblast proliferation promoting effect and a high collagen production promoting effect as compared with a composition prepared by merely adding an ascorbic acid or a derivative thereof to a protease degradation product prepared in the absence of such an ascorbic acid, an ascorbate or a salt thereof.

The amount of the ascorbic acid, ascorbate or salt thereof to be added to the composition is preferably 0.5 to 40% by mass relative to the total amount of the composition after the addition, or a solution of the composition or a suspension of the composition, more preferably 0.7 to 20% by mass, even more preferably 1 to 10% by mass, and especially preferably 1 to 5% by mass. In the case where two or more kinds of an ascorbic acid, an ascorbate or a salt thereof are added to the composition, the total amount thereof is the above-mentioned "amount of the ascorbic acid, ascorbate or salt thereof to be added to the composition". Here, when the added amount is relatively large, preferably, a pH regulating agent is added to the composition, or using a salt of an ascorbic acid or a salt of an ascorbate, the pH of the composition is preferably controlled to fall within a range of 6 to 8. Regarding the addition mode of the ascorbic acid, ascorbate or salt thereof, the amount thereof to be added may be divided into small portions and the portions may be added gradually and little by little, or all the amount thereof to be added may be added at a time.

[Protease]

The kind of the protease to be used for degrading the above-mentioned composition in the present invention is not specifically limited. Any protease usable for ordinary proteolysis is usable here. Specifically, an endopeptidase or an exopeptidase is usable, and the active site may be any of serine, cystine, metal, aspartic acid, etc. Plural proteases may be mixed and used here. As a preferred protease, for example, a pronase may be used.

[Production Example for Protease Degradation Composition]

Next, the production method for a protease degradation composition of the present invention is described concretely with reference to a case of using a comb as the composition containing a hyaluronic acid and a protein.

The production method for a protease degradation composition of the present invention includes a step of degrading a composition containing a hyaluronic acid and a protein with a protease, in the presence of an ascorbic acid, an ascorbate or a salt thereof, and may optionally include any other step. For example, in the case where the composition is a comb, the production method may have a chipping step of chipping a comb, prior to the enzyme treatment step. In addition, the production method may have, after the enzyme treatment step, a filtration step of filtrating the degradation composition, a powdering step of drying and grinding the filtrated degradation composition, and a purification step of purifying the filtered degradation composition. In the following, examples of the production method for a protease degradation composition of the present invention are described in detail.

First, a composition containing a hyaluronic, acid and a protein is prepared. In the case where a cock's comb is used as the composition, any one is usable irrespective of age and sex. Preferably, however, a cock's comb is processed for protease degradation shortly after its collection. In the case where a cock's comb is processed for protease degradation long after its collection, preferably, it is once freeze-dried and then thawed before use.

In protease degradation of a comb in the presence of an ascorbic acid, an ascorbate or a salt thereof, preferably, the comb is first processed in a chipping step of chipping it, then an ascorbic acid, an ascorbate or a salt thereof is added to the resultant comb pieces, and the comb pieces are brought into contact with a protease-containing solution. The comb is preferably chipped into pieces of 0.5 cm square or more, more preferably 0.7 cm square or more, even more preferably 0.9 cm square or more. If too much chipped or minced, water may excessively flow out of the resultant pieces, unfavorably.

Next, an ascorbic acid, an ascorbate or a salt thereof is added to and mixed with the composition, and in the presence of the added substance, the composition is processed in an enzyme treatment step of degrading it with a protease. Regarding the ascorbic acid, ascorbate or salt thereof, and the preferred ranges and the specific examples thereof, the description in the column of [Ascorbic Acid, Ascorbate or Salt Thereof] given hereinabove may be referred to. Regarding the condition for adding the substance, the description in the column of [Condition in Adding Ascorbic Acid, Ascorbate or Salt Thereof] may be referred to. Regarding the description of protease, the description in the column of [Protease] given hereinabove may be referred to. The mode of adding an ascorbic acid, an ascorbate or a salt thereof to the composition and mixing it with the composition may vary depending on the kind of the composition and the protease, but for example, in the case where the composition is a solid or a powder of a comb or the like, preferably, a solution prepared by dissolving an ascorbic acid, an ascorbate or a salt thereof is added to and mixed with the composition prior to enzymatic treatment. The enzymatic treatment also varies depending on the kind of the composition and the protease, but for example, in the case where the composition is a solid or a powder of a comb or the like, preferably, a solution such as an aqueous solution of a protease (enzyme solution) is added to the mixture prepared by mixing an ascorbic acid, an ascorbate or a salt thereof with the composition, and then the resultant mixture is kept as such for a while for enzymatic treatment. Here, the pH of the enzyme solution is preferably 5.0 to 10.0, the treatment temperature is preferably 40 to 60° C., and the treatment time is preferably 0.5 to 3.0 hours. Also preferably, the enzyme treatment is carried out while the composition to which the enzyme solution has been added is shaken.

From the protease degradation composition obtained in the manner as above, a solid fraction of combs and others may be removed through filtration or the like, and the resultant liquid may be used as a liquid protease degradation composition. If desired, the degradation composition may be further processed in a powdering step of drying it by freeze-drying or the like followed by further grinding it to give a powdery protease degradation composition for actual use.

The production method for a protease degradation composition of the present invention is an extremely simple process as above, and can provide a protease degradation composition having a high fibroblast proliferation promoting effect and a high collagen production promoting effect, at low cost.

In addition, by purifying the filtered protease degradation composition or the powdery protease degradation composition, a composition having a higher fibroblast proliferation promoting effect and a higher collagen production promoting effect can be provided. For the purification method for the degradation composition, an ordinary purification method of liquid-liquid separation, column chromatography or the like may be employed.

<Composition>

Next, the composition of the present invention is described below.

The composition of the present invention is produced according to the production method for a protease degradation composition of the present invention.

Regarding the description of the production method for a protease degradation composition of the present invention, the description in the column of <Production Method for Protease Degradation Composition> given hereinabove may be referred to.

In the following, the ingredients that the composition of the present invention contains and the content thereof are described. In the following description, the composition (composition containing a hyaluronic acid and a protein) to be used as the raw material in the production method for a protease degradation composition of the present invention may be referred to as "raw material composition" to be differentiated from the composition produced according to the production method of the present invention.

The composition of the present invention is one obtained according to the production method for a protease degradation composition of the present invention, and therefore contains a protease degradation composition produced through degradation of a composition containing a hyaluronic acid and a protein with a protease in the presence of an ascorbic acid, an ascorbate or a salt thereof. Here, the protease degradation composition contains at least a protein-degraded product that has been degraded with a protease, and a hyaluronic acid, and may contain an ascorbic acid, an ascorbate or a salt thereof that has been made to exist during the degradation reaction, an undegraded protein (a protein naturally contained in the composition before protease addition thereto) and any other component derived from the raw material composition.

The protein-degraded product contained in the protease degradation composition includes a protein, a peptide and a free amino acid having a lower molecular weight than that of the undegraded protein, and these may exist in the degradation composition as mixed therein.

Preferably, the protease degradation composition contains a free amino acid. The free amino acid that the degradation composition contains may be a free amino acid as a protein-degraded product, or a free amino acid naturally contained in the composition before protease addition thereto. The kind of the free amino acid varies depending on the components of the composition. For example, in the protease degradation composition from a composition of a comb, amino acids such as isoleucine, β-aminoisobutyric acid, alanine, phenylalanine, aspartic acid, cystine and tyrosine are contained in a relatively high content, and in addition to these, other various kinds of amino acids are contained therein.

The total protein amount in the composition of the present invention is preferably 0.5 to 10% by mass as a ratio by mass to the total amount of the composition, more preferably 1 to 7% by mass, even more preferably 2 to 5% by mass. The total free amino acid amount in the composition of the present invention is preferably 0.5 to 12% by mass as a ratio by mass to the total amount of the composition, more preferably 1 to 8% by mass, even more preferably 2 to 6% by mass. When the total protein amount and the free amino acid amount in the composition of the present invention each fall within the above-mentioned range, the composition is considered to effectively act so as to noticeably exhibit a fibroblast proliferation promoting effect and a collagen production promoting effect.

In this description, the "total protein amount" means a total protein content determined according to a Lowry method; and the "total free amino acid amount" is a total amount of free amino acids determined according to a Ninhydrin method.

The hyaluronic acid contained in the protease degradation composition may be the hyaluronic acid that has been naturally contained in the raw material composition before protease addition and has remained therein as such (hereinafter referred to as "undegraded hyaluronic acid"), or a degradation product of a hyaluronic acid (hereinafter referred to as "low-molecular hyaluronic acid"), or a mixture of the undegraded hyaluronic acid and the low-molecular hyaluronic acid, and preferably, the degradation product contains a low-molecular hyaluronic acid. A low-molecular hyaluronic acid can readily penetrate into the depth of a living organism and can effectively act on a living organism. In the case where the protease degradation composition contains a low-molecular hyaluronic acid, the low-molecular hyaluronic acid may be a low-molecular hyaluronic acid obtained by hydrolyzing the hyaluronic acid in the raw material composition, or may also be a low-molecular hyaluronic acid prepared by hydrolyzing a hyaluronic acid in a system different from the raw material composition and adding the resultant low-molecular hyaluronic acid to the degradation composition. Preferably, a low-molecular hyaluronic acid obtained by hydrolyzing the hyaluronic acid in the raw material composition is contained in the degradation composition. For producing a low-molecular hyaluronic acid in the raw material composition, a substance capable of hydrolyzing a hyaluronic acid, such as hydrochloric acid or hyaluronidase may be added to the raw material composition in which the hyaluronic acid is to be hydrolyzed. In the case where the raw material composition is a natural substance, a low-molecular hyaluronic acid may be produced through autolysis with a substance originally contained in the natural substance. However, from the viewpoint of effectively realizing the action of a hyaluronic acid on a living organism, preferably, the hyaluronic acid maintains the structural unit thereof, that is, the hyaluronic acid is not degraded to glucuronic acid and N-acetyl glucosamine. Specifically, the N-acetylglucosamine content in the composition of the present invention is preferably 0.01% by mass or less relative to the total amount of the composition, and is most preferably 0% by mass.

In this description, the "N-acetylglucosamine amount" is an N-acetylglucosamine content determined according to a Morgan-Elson method.

The molecular weight of the low-molecular hyaluronic acid that the protease degradation composition contains is preferably 380 to 5000. The molecular weight of 380 to 5000 corresponds to about 1 to 14 recurring units of hyaluronic acid. The content of the low-molecular hyaluronic acid having a molecular weight of 380 to 5000 in the composition of the present invention is preferably 5% by mass or more relative to the total amount of the composition, more preferably 7% by mass or more, even more preferably 10% by mass or more. Preferably, the main component of the low-molecular hyaluronic acid is a low-molecular hyaluronic acid having a molecular weight of 1520 to 5000, more preferably the proportion of a low-molecular hyaluronic acid having a molecular weight of 1520 to 5000 is 60% by mass or more of the total amount of the low-molecular hyaluronic acid having a molecular weight of 380 to 5000, even more preferably 70% by mass or more, and further more preferably 75% by mass or more. With that, it is considered that the composition of the present invention can effectively act to noticeably exhibit a fibroblast proliferation promoting effect and a collagen production promoting effect.

The molecular weight and the mass ratio of the low-molecular hyaluronic acid can be determined through analysis of high-performance liquid chromatography using polyethylene glycol as a molecular weight marker.

The protease degradation composition generally contains an ascorbic acid, an ascorbate or a salt thereof that has been made to exist therein in degradation reaction. The content of the ascorbic acid, ascorbate or salt thereof in the composition of the present invention is preferably 0.5 to 40% by mass relative to the total amount of the composition, more preferably 1 to 10% by mass, and even more preferably 3 to 5% by mass.

In this description, the content of the ascorbic acid, ascorbate or salt thereof means a content thereof determined according to HPLC (high-performance liquid chromatography).

The properties of the protease degradation composition vary depending on the components and the composition ratio of the raw material composition and the kind of the protease to be used. In general, the degradation product is liquid, precisely viscous liquid. The protease degradation composition may be used as the composition of the present invention directly as it is, but may be suitably purified and combined with any other component to be the composition of the present invention. By purifying the protease degradation composition, a composition having a higher fibroblast proliferation promoting effect and a higher collagen production promoting effect can be provided. A liquid composition can be used as an external preparation for external application or ocular instillation, or as an internal preparation of a type of drink. In the case where the protease degradation composition is dried by freeze drying or the like and then ground, a powdery composition can be provided. The powdery composition can be used as an internal preparation directly as it is, or after mixed with any other component, or may be processed into tablets or capsules, or a desired solvent or dispersion medium may be added thereto to form a liquid, and the resultant liquid may be used as an external preparation for external application or ocular instillation, or as an internal preparation of a type of drink.

As in the above, the composition of the present invention may be provided in any form capable of exhibiting a fibroblast proliferation promoting effect and a collagen production promoting effect. For example, the composition may be provided as medicines stated clearly to have these pharmaceutical potencies, quasi-drugs, functional foods (including supplementary foods, health foods, candies, chewing gums), functional drinks (including jelly drinks, solid-containing liquid drinks), functional cosmetics, and supplements, and these embodiments in use are interpreted to be included in the scope of the "composition" of the present invention.

The composition of the present invention may contain any other various components than the above-mentioned protease degradation composition. For example, in the ease where a vehicle is added to the composition, the blend ratio of the degradation product and the vehicle may be controlled to thereby control the component amount such as the total protein amount, the total free amino acid amount and the low-molecular hyaluronic acid amount. An embodiment of the composition that is easy to store is a mixture powder produced by diluting a ground powder of a freeze-dried degradation composition with a vehicle. The vehicle is not specifically limited, but is preferably dextrin. The dilution ratio with the vehicle is preferably 2 to 10 times as a ratio by mass, more preferably 2 to 7 times, even more preferably 3 to 5 times.

The composition of the present invention has a fibroblast proliferation promoting effect and a collagen production promoting effect. Accordingly, in the ease where the composition of the present invention is taken orally and where the components thereof are absorbed by the intestinal tract, the composition effectively improves fibroblast proliferation and collagen production at the dermis and the wounded site where the composition has arrived. As a result, the conditions of skin tenseness and elasticity can be improved and healing of wounded sites can be promoted. Here, the composition of the present invention is highly safe as using a hyaluronic acid and a protein that are biogenic substances and an enzyme that reacts mildly, and therefore has an advantage in that the composition can be used as an internal preparation to be taken orally with ease.

The amount of the composition of the present invention to be used varies depending on the targeted failure and is, for example, the following dose is preferred.

For example, in the case where the composition of the present invention is orally administered as an internal preparation, the dose thereof is preferably 80 to 2000 mg/adult standard body weight/day, and multiple dosage of two or three times a day is suitable. The dose of the protease-degraded product is preferably 1 to 1500 mg/adult standard body weight/day.

[Use of Composition]

As described above, the composition of the present invention has a fibroblast proliferation promoting effect and a collagen production promoting effect. Consequently, the composition of the present invention can be administered to animals including human beings and can be effectively used as a fibroblast proliferation promoting agent for promoting the proliferation of fibroblasts and as a collagen production promoting agent for promoting collagen production by fibroblasts. In addition, the composition may be used as a medicine having these effects as combined. The composition as an internal preparation may optionally contain any other various components than the above-mentioned degradation composition and vehicle. For example, vitamins, vegetable powders, minerals, yeast extracts, colorants and tackifiers may be optionally added thereto. The kind of these components is not specifically limited, and the content thereof may be appropriately controlled within a range capable of sufficiently exhibiting the intended function.

Examples

The present invention is described more specifically with reference to Examples given below. The materials, the ratio thereof and the operations in the following Examples may be appropriately varied not overstepping the scope and the spirit of the present invention. Accordingly, the range of the present invention should not be interpreted limitatively by the specific examples shown below.

Component analysis of the compositions produced in this Example was carried out according to the following methods.

(1) Measurement of Water Content

One g of the composition was heated and dried at 105° C. for 3 hours, and the constant weight thereof was measured with a precision balance to quantify the water content thereof.

(2) Total Nitrogen Determination

The total nitrogen was quantitatively determined according to a semimicro-Kjeldahl method based on an AOAC method.

(3) Free Amino Acid Determination and Amino Acid Composition Analysis

The total free amino acid amount was quantified according to a Ninhydrin method. For quantification, a calibration curve of leucine as a standard amino acid was formed and used. The composition of the free amino acid was analyzed using an amino acid automatic analyzer (manufactured by Hitachi Limited, L-8500 Model) equipped with a column for bioanalysis. In the analysis, 50 mg of the composition was dissolved in distilled water, dried into solid under reduced pressure using a rotary evaporator (60° C.), then eluted with 5 mL of 0.02 N hydrochloric acid, and filtered through filter paper and then through a germ-free filter, and 50 μL of the resultant filtrate was used as an analysis sample.

(4) Protein Determination

The total protein amount was determined according to a Lawry method. A bovine serum albumin was used for forming a standard calibration curve.

(5) N-acetyl-D-glucosamine Determination

The N-acetyl-D-glucosamine content was determined according to a Morgan-Elson method.

(6) Glucosaminoglycan Determination

The sample was analyzed through colorimetry according to a 2-nitrophenylhydrazine coupling method. For standard calibration curve formation, comb-derived sodium hyaluronate (manufactured by Wako Pure Chemical Corporation, HARC) and Streptococcus zooepidemicus-derived sodium hyaluronate (manufactured by Wako Pure Chemical Corporation, HASZ) were used.

(7) Measurement of Molecular Weight of Low-Molecular Hyaluronic Acid

The molecular weight of hyaluronic acid was estimated through high-performance liquid chromatography (by Shimadzu Corporation) equipped with a differential refractometer (manufactured by Shimadzu Corporation, RID-10A Model). Columns of TSKgel G-2, 500PW$_{XL}$ (7.8 mm ID×30 cm) were used, and water was used as a mobile phase at a flow rate of 1 ml/min for analysis. As a molecular weight marker, four types of polyethylene glycol having a molecular weight of 400, 1000, 2000 or 6000 (manufactured by Aldrich Corp.) were used. The constituent weight ratio of each low-molecular hyaluronic acid was analyzed through high-performance liquid chromatography using samples of the pharmaceutical composition or dextrin alone, in which the peak area of dextrin was detracted from the peak area of the composition to determine the constituent weight ratio.

Production Example

One kg of freshly collected cock's combs were cut into small pieces of about 0.5 to 2.0 cm square, and thermally sterilized by steaming at 100° C. A solution of L-ascorbic acid 2-glucoside was added to and fully mixed with the small pieces. At this time, the amount of L-ascorbic acid 2-glucoside added was so controlled to be 3.56% by mass of the amount of the freeze-dried powder to be mentioned below. Subsequently, food-derived enzymes mainly containing a protease were added to the mixture of the combs and the L-ascorbic acid 2-glucoside solution and reacted at 45° C. for 1.5 hours, and then stirred and homogenized. Subsequently, rough solid fragments were removed by filtration to give a liquid protease degradation composition. The protease degradation composition had a pH of 6.5, a Brix value of 6.20 and a solid concentration of 5.91% by mass. The protease degradation product was freeze-dried and ground to be a freeze-dried powder of protease degradation composition. An equal amount (as a ratio by mass) of dextrin was added to the freeze-dried powder of protease degradation composition to give a dextrin-added freeze-dried powder (composition 1).

[Component Analysis of Composition]

The produced composition 1 was analyzed for the constituent components thereof according to the above-mentioned method. The content of general components analyzed is shown in Table 1, the composition of free amino acids is shown in Table 2, and the analysis results of molecular weight of low-molecular hyaluronic acids are shown in Table 3. In Tables 1 to 3, "%" is "% by mass".

TABLE 1

| General Components | |
| --- | --- |
| | % |
| Water | 2.2-2.6 |
| Nitrogen | 3.84 |
| Total Protein | 3.04 |
| Free Amino Acid | 4.08 |
| N-acetylglucosamine | 0 |
| Dextrin (for food additive) | 75.0 |

TABLE 2

| Free Amino Acid Composition | | | |
| --- | --- | --- | --- |
| Amino Acid | Content % | Amino Acid | Content % |
| ρ-serine | 1.71 | Cystine* | 2.78 |
| Taurine | 3.30 | Leucine* | 2.26 |
| Aspartic Acid* | 2.94 | Isoleucine* | 6.27 |
| Threonine* | 1.30 | Tyrosine* | 2.65 |
| Serine* | 2.20 | Phenylalanine* | 3.30 |
| Glutamic Acid* | 2.18 | β-aminoisobutyric Acid | 5.45 |
| Glutamine | 0.48 | Ornithine | 1.05 |
| Sarcosine | 1.81 | Lysine* | 1.17 |
| Glycine* | 2.26 | 1-Methylhystidine | 0.78 |
| Alanine* | 3.52 | Anserine | 1.92 |
| Citrulline | 0.92 | Arginine* | 1.93 |
| α-Aminobutyric Acid | 2.18 | Identified Total Amino Acids | 57.36 |

TABLE 2-continued

Free Amino Acid Composition

| Amino Acid | Content % | Amino Acid | Content % |
|---|---|---|---|
| Cystine* | 1.03 | Unknown Amino Acids | 42.64 |
| Methionine* | 1.97 | | |

*Protein constituent amino acid

TABLE 3

Estimated Molecular Weight, Constituent Unit Number and Constituent Weight Ratio of Low-Molecular HA

| | Peak No. | | | | |
|---|---|---|---|---|---|
| | 1 | 2 | 3 | 4 | 5 |
| Estimated Molecular Weight | 5,000 | 1,520 | 1,140 | 760 | 380 |
| Constituent Unit Number | 13-14 | 4 | 3 | 2 | 1 |
| Constituent Weight Ratio (%) | 33 | 47 | 10 | 6 | 4 |

As shown in Table 2, among the free amino acids contained in the composition 1, the content of isoleucine and β-aminoisobutyric acid was high, and then, alanine, phenylalanine, aspartic acid, cystine and tyrosine were contained much.

As shown in Table 3, the composition 1 contained five types of low-molecular hyaluronic acids each having an estimated molecular weight of 5000, 1520, 1140, 760 and 380. When the molecular weight of one recurring unit of hyaluronic acid is about 400, the recurring unit number of each low-molecular hyaluronic acid is 13 to 14, 4, 3, 2 and 1 in that order from the largest molecular weight, and the mass ratio was 33%, 47%, 10%, 6% and 4%. Accordingly, it is known that the main components of the low-molecular hyaluronic acids are two components of a 4-molecular component having a molecular weight of about 1520, and a 13 to 14-molecular component having a molecular weight of about 5000. The content of the low-molecular hyaluronic acids having a molecular weight of 380 to 5000 in the composition 1 was 114% by mass relative to the total amount of the composition 1.

<Evaluation of Composition>

In this Example, the composition 1 produced in the above-mentioned Production Example was used as a test substance, and this was tested in a fibroblast proliferation test and a collagen production promotion test to evaluate the effects thereof.

The cells, the reagents and the culture media used in the test are shown below.

[Cells, Reagents, Media]

(1) Cells for Test

As the cells for test, adult-derived normal human fibroblasts bought from Kurabo Industries Ltd. were used.

(2) Reagents

Penicillin-streptomycin mixed solution (manufactured by Nacalai Tesque, Inc.)

DMEM (Dulbecco's modified Eagle medium, manufactured by Nacalai Tesque, Inc.)

FBS (fetal bovine serum, manufactured by Cell Culture Bioscience)

Reagent for measuring the number of living cells, SF (manufactured by Nacalai Tesque, Inc.)

Human collagen type 1 ELISA kit (manufactured by ACEL, Inc.)

(3) Culture Media

As a cell growth medium, DMEM added with 10% FBS and 1 penicillin-streptomycin mixed solution was used; and as a test medium, DMEM added with 1% FBS and 1% penicillin-streptomycin mixed solution was used.

[Comparative Samples]

In this Example, a comparative composition 1 prepared in the same manner as that for the composition 1 except that L-ascorbic acid 2-glucoside was not used, a comparative composition 2 prepared by adding L-ascorbic acid 2-glucoside to the comparative composition 1 in an concentration of 1.78%, and L-ascorbic acid 2-glucoside were used as comparative samples.

[Test Methods]

(1) Preculture of Cells

Adult-derived normal human fibroblasts were sown and initiated in a cell growth medium inside a cell culture flask (Corning's T-75), and cultured in a moist environment at 37° C. in the presence of 5% $CO_2$. During this, the medium was replaced every other day, and at the time when the culture reached 80% confluent growth, the cells were collected and used in the following tests.

(2) Fibroblast Growth Test

The cultured fibroblasts were sown in a 96-well plate to be $5 \times 10^3$ cells/0.1 mL/well, and cultured therein at 37° C. in the presence of 5% $CO_2$ for 1 day. Subsequently, the cell growth medium in each well was replaced with each test medium added with the composition 1, the composition 1 or 2, or L-ascorbic acid 2-glucoside, or with a test medium not added with them (control medium). At this time, the final concentration of the composition 1, or the comparative composition 1 or 2 in each well was 1 mg/mL, 0.1 mg/mL or 0.01 mg/mL. Subsequently, the cells were cultured at 37° C. in the presence of 5% $CO_2$ for 1 day. After the culture, the number of the living cells in each well was counted, and apart from these, the cells were cultured at 37° C. in the presence of 5% $CO_2$ for 3 days, and after the culture, the number of the living cells in each well was counted. Here, the number of the living cells was counted according to a wst-8 method using a cytometric reagent for living cells. The same test was repeated for a total of 5 times for determining a mean value and a standard error.

Figure 2:
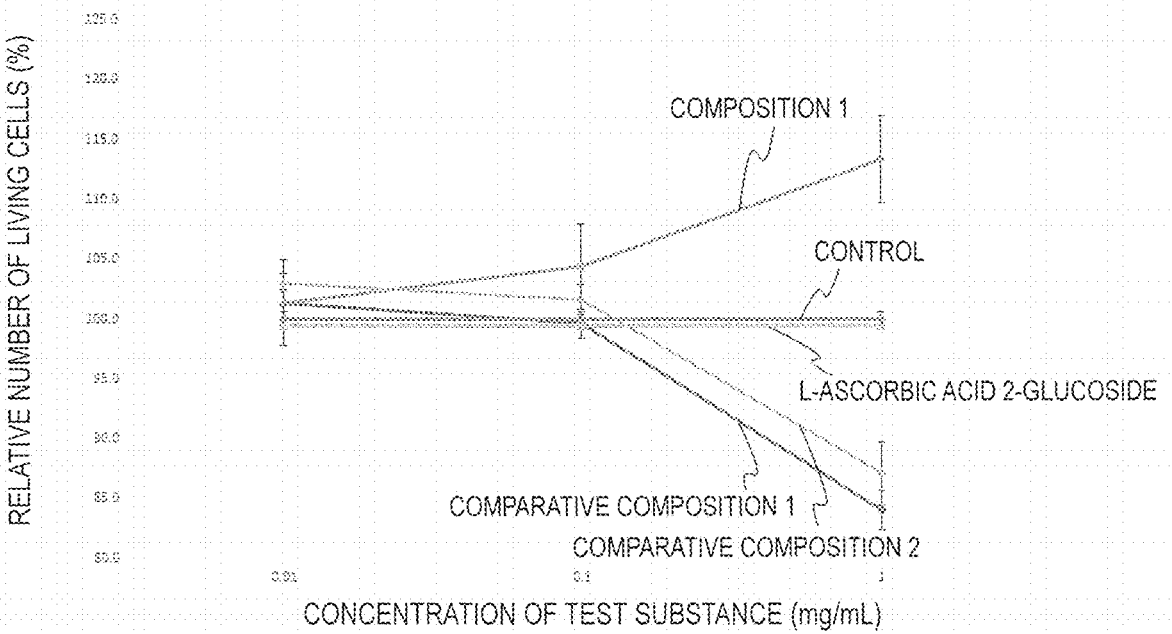
FIG. 2 is a graph showing a relative number of living cells after culture of human fibroblasts for 3 days in a medium added with the composition 1, the comparative composition 1 or 2 or L-ascorbic acid 2-glucoside.

Results of relative cytometry for living cells in one day after addition of each test medium are shown in FIG. 1; and results of relative cytometry for living cells in 3 days after addition of each test medium are in FIG. 2. In FIGS. 1 and 2, "relative number of living cells" is a relative value of the living cells in each test medium, as calculated based on the number of the living cells in the control medium, 100%, and is expressed as a mean value±standard error. In the two-sided Student's t-test, a probability p of less than 0.05 was judged to show a significant difference. In FIGS. 1 and 2, "*" indicates p<0.05, "" indicates p<0.01, and "*" indicates p<0.001.

As shown in FIGS. 1 and 2, the test medium with the comparative composition 1 containing a protease degradation product produced in the absence of ascorbic acid 2-glucoside did not show any significant difference in the number of the living cells relative to the control medium after culture for 1 day, and after culture for 3 days, the number of the living cells in the test medium with the comparative composition 1 rather decreased than in the control medium. In the test medium with the comparative composition 2 prepared by adding ascorbic acid 2-glucoside to the comparative composition 1, the number of the living cells increased a little after culture for 1 day as compared with that in the control medium, but after culture for 3 days, the number of the living cells in the medium with the comparative composition 2 decreased than in the control medium.

On the other hand, in the test medium with the composition 1 containing a protease degradation composition obtained in the presence of ascorbic acid 2-glucoside, a noticeable increase in the number of the living cells recognized both after culture for 1 day and after culture for 3 days, as compared with the control medium. From this, the composition 1 is confirmed to have an extremely high fibroblast proliferation promoting effect.

(3) Collagen Production Promoting Test

The cultured fibroblasts were sown in a 96-well plate to be $5 \times 10^3$ cells/0.1 mL/well, and cultured therein at 37° C. in the presence of 5% $CO_2$ for 1 day. Subsequently, the cell growth medium in each well was replaced with each test medium added with the composition 1 or L-ascorbic acid 2-glucoside, or with a test medium not added with them (control medium). At this time, the final concentration of the composition 1 or L-ascorbic acid 2-glucoside in each well was 1 mg/mL. Subsequently, the cells were cultured at 37° C. in the presence of 5% $CO_2$ for 3 days, then the supernatant of the test medium in each well was collected, and using a human collagen-type 1 ELISA kit, the I-type collagen concentration in the supernatant was measured. The same test was repeated for a total of 5 times for determining a mean value of the collagen concentration. The results are shown in Table 4.

TABLE 4

| Test Substance | Collagen Production Amount (μg/mL) |
|---|---|
| Not added (control) | 1.29 |
| Composition 1 | 5.62 |
| L-ascorbic Acid 2-Glucoside | 4.29 |

As shown in Table 4, in the test medium with the composition 1 containing a protease degradation composition obtained in the presence of ascorbic acid 2-glucoside, the collagen concentration is remarkably higher than that in the control medium, and is even higher than that in the test medium with ascorbic acid 2-glucoside. From this, the composition 1 is also confirmed to have a high collagen production promoting effect.

INDUSTRIAL APPLICABILITY

According to the present invention, there can be provided a composition having a high fibroblast proliferation promoting effect and a high collagen production promoting effect at low cost. Consequently, according to the present invention, there can be provided medicines that are expected to effectively promote wound healing and to exhibit an effect of improving skin conditions at low cost. Accordingly, the industrial applicability of the present invention is great.

What is claimed is:

1. A method for producing a protease degradation composition by degrading a composition containing a hyaluronic acid and a protein with a protease, in the presence of an ascorbic acid, an ascorbate or a salt thereof in an amount of 0.5% to 40% by mass.

2. The production method according to claim 1, wherein the composition containing a hyaluronic acid and a protein is a comb.

3. The production method according to claim 1, wherein as the ascorbic acid, ascorbate or salt thereof, one in which the hydrogen atom of the 2-positioned hydroxy group is substituted with a glycosyl group is used.

4. The production method according to claim 1, including a step of adding the ascorbic acid, ascorbate or salt thereof to the composition.

5. The production method according to claim 4, wherein the amount of the ascorbic acid, ascorbate or salt thereof added to the composition is 0.5 to 40% by mass relative to the total amount of the composition after the addition.

6. The production method according to claim 4, wherein the ascorbic acid, ascorbate or salt thereof is added before the composition is brought into contact with a protease.

7. The production method according to claim 6, in which the composition containing a hyaluronic acid and a protein is a comb, and which includes:
a step of chipping the comb into pieces of 0.5 cm square or more, a step of adding an ascorbic acid, an ascorbate or a salt thereof to the comb pieces and mixing them to give a mixture, and a step of adding a protease to the mixture to thereby degrade the comb pieces with the protease.

* * * * *